(12) United States Patent
Yang

(10) Patent No.: US 6,539,810 B2
(45) Date of Patent: Apr. 1, 2003

(54) METHOD OF ESTIMATING TENSILE PROPERTIES OF IN718 CAST HIPED COMPONENTS

(75) Inventor: Ling Yang, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 133 days.

(21) Appl. No.: 09/742,444

(22) Filed: Dec. 22, 2000

(65) Prior Publication Data

US 2002/0117008 A1 Aug. 29, 2002

(51) Int. Cl.[7] .................................................. G01N 3/08
(52) U.S. Cl. ............................... 73/826; 73/760; 73/789
(58) Field of Search ........................... 73/781–807, 760, 73/826; 148/128, 421, 677

(56) References Cited

U.S. PATENT DOCUMENTS

| | | | | | |
|---|---|---|---|---|---|
| 3,964,938 | A | * | 6/1976 | Tolliver et al. | 148/12 B |
| 5,374,323 | A | * | 12/1994 | Kuhlman et al. | 148/677 |
| 5,492,574 | A | * | 2/1996 | Huang | 148/421 |

* cited by examiner

Primary Examiner—Hezron Williams
Assistant Examiner—Monica D. Harrison
(74) Attorney, Agent, or Firm—Banner & Witcoff, Ltd.

(57) ABSTRACT

A method to estimate the tensile properties of HIPed cast IN718 components at various grain sizes and different operating temperatures by using transfer functions to estimate ultimate tensile strength, yield strength, and elongation.

9 Claims, 1 Drawing Sheet

METHOD OF ESTIMATING TENSILE PROPERTIES OF IN718 CAST HIPED COMPONENTS

BACKGROUND OF THE INVENTION

1. Field of the Invention

This invention relates to a method for estimating tensile properties of IN718 cast HIPed material.

2. Description of the Prior Art

Inconel Alloy 718 (IN718) has the major chemistry of Ni—Fe—Cr—Cb—Mo—Ti—Al and was developed through extensive optimization studies by H. L. Eiselstein at the International Nickel Company (INCO) in the 1950's. Alloy IN718 is a precipitation hardenable nickel based alloy with high strength and ductility at temperatures up to 704° C., good corrosion resistance, ease of formability and can be welded with good resistance to strain-age cracking. Alloy IN718 was initially developed for the aerospace industry, and it has been used for jet engine and high-speed airframe parts such as wheels, buckets, spacers, and high temperature bolts and fasteners. IN718 investment cast HIPed material is a new approach in making manifold for steam delivery system in GE H technology gas turbines.

Investment casting, often called lost wax casting, is regarded as a precision casting process to fabricate near-net-shaped metal parts from almost any alloy. The most common use of investment casting in more recent history has been the production of components requiring complex, often thin-wall castings. The investment casting process normally includes the following steps: creating a wax pattern, assembling a wax pattern cluster, "investing" a cluster with ceramic stucco/slurry; de-waxing and fire molding the ceramic for strength, melting the alloy in vacuum or air; pouring molten alloy into the mold; knocking off the shell and heat treating/machining/coating operations. An HIP process (Hot Isostatic Pressing) sometimes follows the investment casting process to consolidate shrinkage porosity internal to the casting and help homogenize the structure.

GE Power Systems introduced H technology gas turbines in 1995. H technology is a platform of combined-cycle technology that integrates the gas turbine, steam turbine, and generator into a seamless system, where each component is optimized for the highest level of performance. The centerpiece of this new technology platform is an advanced closed-loop steam cooling system in the gas turbine. This cooling system permits higher firing temperature while retaining combustion temperatures at levels consistent with low emissions. This enables the new machines to operate at firing temperatures in the 2,600F class, leading to 60% net thermal efficiency and world record output for a combined-cycle unit. Unlike aircraft engines, which only have air for cooling, a combined-cycle system has a ready steam supply. The steam is captured and used for cooling in this closed-loop system. Steam is desired because it has a higher heat capacity than air. The steam cooling system uses a manifold as a critical component. However, it is difficult to make the manifold due to its complex geometry. See FIG. 1.

Originally, manifolds were made by machining forged alloy IN718 material to the desired shape. This process can be expensive and take a long time. Other processes were investigated to reduce the cost and cycle time. One process, HIPed (Hot Isostatic Press) investment casting process, was considered. Manifolds produced by the investment cast process of alloy IN718 have lower costs, larger yields and reduced cycle time.

Forging produces a better tensile property than casting at the same grain size since forging can produce a uniform grain size distribution in the IN718 material. Casting, on the other hand, produces an IN718 material having a wide range of grain sizes. However, in order to design and form the manifold with the HIPed investment casting process, tensile strength and ductility must be considered. These properties are usually identified by ultimate tensile strength, yield strength, and elongation. However, heretofore these properties were not directly measurable for alloy IN718 products formed by the HIPed investment cast process, rendering design of the manifold difficult.

Tensile properties can be affected by many factors, such as process parameters, grain size, and temperature. Materials made by investment casting can have varied grain sizes. For example, thin sections or areas close to the mold can have fine grains, while the center of thick sections can have coarse grain size.

Due to its manufacturing history and the lack of property data, the tensile properties of cast alloy IN718 has been estimated by using the Grain Size 3 Forging—3σ rule. This rule calculates the average value of forging material with grain size ASTM3 and calculates the standard deviation a, shift the average curve down by 3σ, curve obtained is called −3σ curve. Some skilled in the art sometimes use a different level of conservative (for example, a −2σ curve) for different applications. Although, this forging rule has been used to estimate tensile properties for casting materials, estimating tensile properties of forging materials is more accurate than casting materials.

As discussed above, the forging property data having a grain size of ASTM 3 was parallel shifted down by three times its standard deviation, and the correspondent new curve was used for the design basis for the HIPed investment cast IN718 manifold. However, this rule did not provide accurate results because the same value was assumed for all grain sizes. That is, it was assumed that the tensile properties: yield strength, elongation, etc., were dependent only on temperature, not grain size. This is not accurate. Therefore, designing and forming the manifold with cast HIPed IN718 material has been difficult because of the less than accurate tensile data available.

BRIEF SUMMARY OF THE INVENTION

The invention is directed to a method to estimate the tensile properties of HIPed cast IN718 components at various grain sizes and different operating temperatures. The invention uses transfer functions to estimate ultimate tensile strength, yield strength, and elongation.

In particular, the invention is directed to a method of estimating ultimate tensile strength (UTS) of a cast HIPed IN718 component with known local grain size and operating temperature by solving the following equation:

$$UTS = (238.3 - 19.44 \times GS + 3.355 \times GS^2 - 0.0889 \times (T-32) + 2.28 \times 10^{-5} \times (T-32)^2 - 4.39 \times 10^{-4} \times GS \times (T-32)) \times 7 \times 10^6$$

whereby GS is the average grain size in meters, T is temperature in degree C., and UTS is in the unit of Pascal.

The invention is further directed to a method of estimating 0.2% yield strength (0.2% YS) of a cast HIPed IN718 component with known local grain size and operating temperature by solving the following equation:

$$0.2\% \ YS = (219.2 - 23.38 \times GS + 4.447 \times GS^2 - 0.089 \times (T-32)) \times 7 \times 10^6$$

whereby GS is the average grain size in meters, T is temperature in degree C., and 0.2% YS is in the unit of Pascal.

The invention is further directed to a method of determining the 0.02% yield strength (0.02% YS) of a cast HIPed IN718 component with known local grain size and operating temperature by solving the following equation:

$$0.02\% \ YS = (130 - 25.04 \times GS + 5.1 \times GS^2 + 5.56 \times 10^{-3} \times (T-32) - 4.44 \times 10^{-4} \times GS \times (T-32)) \times 7 \times 10^6$$

whereby GS is the average grain size in meters, T is temperature in degree C., and 0.02% YS is in the unit of Pascal.

In addition, the invention is directed to a method of determining the elongation (elong.) of a cast HIPed IN718 component with known local grain size and operating temperature by solving the following equation:

$$\text{elong.} = 139.3 + 1.3 \times GS - 1.421 \times GS^2 - 0.128 \times (T-32) + 1.57 \times 10^{-3} GS \times (T-32)$$

whereby GS is the average grain size in meters, T is temperature in degree C., and elongation is in the unit of percentage %.

The estimates obtained from the transfer functions can be used for designing of and predicting the life of cast components such as manifolds.

DETAILED DESCRIPTION OF THE INVENTION

Figure 1:
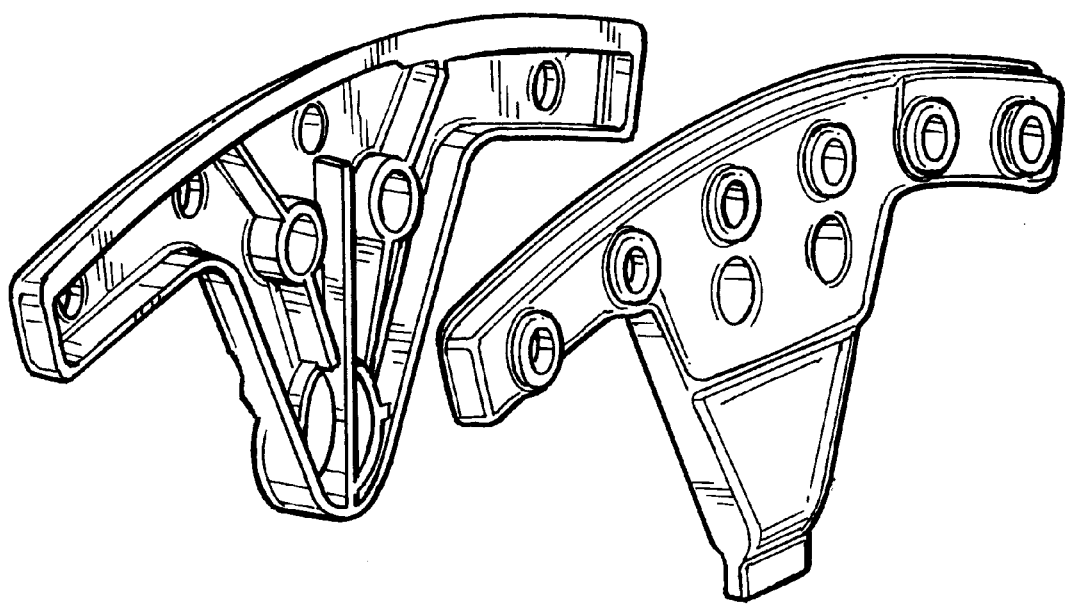
FIG. 1 depicts a manifold.

It was discovered that relationships existed between tensile strength and ductility and the corresponding grain size and operating temperature of HIPed cast IN718 components. When the grain size range of the component and the operating temperature are known, tensile strength and ductility can be estimated. In addition, the minimum tensile strength of the grain size range can be estimated to determine the worst cast condition. These relationships are important in the designing of, and for predicting the life of, the cast components such as manifolds. The relationships are also important in other cast processes such as for the formation of elbows in steam delivery systems. The development of these relationships are described below.

As can be seen in FIG. 1, a manifold has thin walls and a complex geometry making it difficult to machine tensile specimens from the manifold in order to test its properties. Therefore, in order to obtain accurate data easily, slabs of IN718 having a simple geometry were made and tested. Several different superheat temperatures and mold sizes were applied to the slabs to obtain slabs having three different grain diameters, 0.125", 0.050" and 0.029" respectively. This grain size range covers the normal range encountered in manifold production.

| Slab ID | Superheat (F.) | Mold Size | Average Grain Size (") |
|---|---|---|---|
| 1 | 30 | 6.0" × 3.1" × 1.0" | 0.125 |
| 2 | 30 | 4.4" × 4.0" × 0.68"* | 0.050 |
| 3 | 20 | 4.4" × 4.0" × 0.68"* | 0.029 |

*Slab with thinner section in center (grain size in thicker edge sections was 0.050 and in the thinner center section was 0.029").

Multiple specimens were taken from each slab, and tensile testing of the specimens was performed at temperatures of 426° C. (800° F.), 482° C. (900° F.), 538° C. (1000° F.) and 593° C. (1100° F.). This temperature range represents the operating temperature range of the manifold. Results on ultimate tensile strength, yield strength, elongation, reduction of area, 0.2% and 0.02% yield strength and modulus etc. were recorded and analyzed by statistic software Minitab.

From the results, it was observed that (1) tensile strength and ductility increases with the decrease of operating temperature and (2) tensile strength and ductility increases with the decrease of grain size.

Based on the data, the following transfer functions were developed. GS is the average diameter of the grains (inch), and T is the operating temperature (Fahrenheit).

UTS ksi = $238.3 - 765.5 \times GS + 3728.33 \times GS^2 - 0.16 \times T + 7.4 \times 10^{-5} \times T^2 - 0.031 \times GS \times T$ 0.2% YS ksi = $219.2 - 920.6 \times GS + 4941.1 \times GS^2 - 0.16 \times T$ 0.02% YS ksi = $130 - 985.9 \times GS + 5665.9 \times GS^2 + 0.01 \times T - 0.03 GS \times T$ Elong % = $139.3 + 51.2 \times GS - 1578.6 \times GS^2 - 0.23 \times T + 0.111 \times GS \times T$ The transfer functions were then converted to metric units. GS is the average diameter of the grains (meters), and T is the operating temperature (degree C.).

UTS (Pascal) = $(238.3 - 19.44 \times GS + 3.355 \times GS^2 - 0.0889 \times (T-32) + 2.28 \times 10^{-5} \times (T-32)^2 - 4.39 \times 10^{-4} \times GS \times (T-32)) \times 7 \times 10^6$ 0.2% YS = $(219.2 - 23.38 \times GS + 4.447 \times GS^2 - 0.089 \times (T-32)) \times 7 \times 10^6$ 0.02% YS = $(130 - 25.04 \times GS + 5.1 \times GS^2 + 5.56 \times 10^{-3} \times (T-32) - 4.44 \times 10^{-4} \times GS \times (T-32)) \times 7 \times 10^6$ Elong. % = $139.3 + 1.3 \times GS - 1.421 \times GS^2 - 0.128 \times (T-32) + 1.57 \times 10^{-3} \times GS \times (T-32)$ UTS represents the ultimate tensile strength to cause the material rupture. YS represents yield strength, which is the stress necessary to produce significant plastic deformation in a material under uniaxial tensile or compressive load. 0.2% YS and 0.02% YS are the stress at which the material exhibits 0.2% and 0.02% offset strain of plastic deformation respectively. Elong is the percentage of elongation, which represents the ductility of material.

When the grain size of the cast HIPed IN718 material and the operating temperature are known, tensile strength and ductility can be estimated from the transfer functions. Ductility is represented by elongation, and strength is represented by ultimate tensile strength and yield strength.

In order to confirm that the transfer functions provided accurate results, specimens were taken from an actual cast manifold and grain sizes were measured for each specimen. The specimens were tested at the temperature range of 426° C. to 593° C. (800° F. to 1100° F.). The results showed that the transfer function provided accurate results.

This method can determine the tensile properties for the design of the HIPed investment IN718 casting manifold or any other component made of HIPed cast IN718. Given a certain grain size, the minimum tensile properties at high temperature can be estimated. Moreover given an operating temperature and required tensile strength, one can determine the maximum grain size that can be used.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of estimating ultimate tensile strength (UTS) of a HIPed IN718 cast component at an operating temperature comprising solving the following equation using a known average grain size of the component:

$$UTS=(238.3-19.44 \times GS+3.355 \times GS^2-0.0889 \times (T-32)+2.28 \times 10^{-5} \times (T-32)^3-4.39 \times 10^{-4} \times GS \times (T-32)) \times 7 \times 10^6$$

whereby GS is the average grain size in meters, T is temperature in degree C., and UTS is in the unit of Pascal.

2. The method of claim 1 wherein the cast component is a manifold.

3. A method of estimating 0.2% yield strength (0.2% YS) of a HIPed IN718 cast component at an operating temperature comprising solving the following equation using a known average grain size of the component:

$$00.2\% \ YS=(219.2-23.38 \times GS+4.447 \times GS^2-0.089 \times (T-32)) \times 7 \times 10^6$$

whereby GS is the average grain size in meters, T is temperature in degree C., and 0.2% YS is in the unit of Pascal.

4. The method of claim 3 wherein the cast component is a manifold.

5. A method of determining the 0.02% yield strength (0.02% YS) of a HIPed IN718 cast component at an operating temperature comprising solving the following equation using a known average grain size of the component:

$$0.02\% \ YS=(130-25.04 \times GS+5.1 \times GS^2 5.56 \times 10^{-3} \times (T-32)-4.44 \times 10^{-4} \times GS \times (T-32)) \times 7 \times 10^6$$

whereby GS is the average grain size in meters, T is temperature in degree C., and 0.02% YS is in the unit of Pascal.

6. The method of claim 5 wherein the cast component is a manifold.

7. A method of determining the elongation (elong.) of a HIPed IN718 cast component at an operating temperature comprising solving the following equation using a known average grain size of the component:

$$elong.=139.3+1.3 \times GS-1.421 \times GS^2-0.128 \times (T-32)+1.57 \times 10^{-3} \times GS \times (T-32)$$

whereby GS is the average grain size in meters, T is temperature in degree C., and elongation is in the unit of percentage %.

8. The method of claim 7 wherein the cast component is a manifold.

9. A method of estimating grain size for a HIPed IN718 cast component with a desired ultimate tensile strength (UTS) or 0.2% yield strength at an operating temperature comprising solving one of the following equations for GS:

$$UTS=(238.3-19.44 \times GS+3.355 \times GS^2-0.0889 \times (T-32)+2.28 \times 10^{-5} \times (T-32)^2-4.39 \times 10^{-4} \times GS \times (T-32)) \times 7 \times 10^6$$

whereby GS is the average grain size in meters, T is temperature in degree C., and UTS is in the unit of Pascal or $$0.2\% \ YS=(219.2-23.38 \times GS+4.447 \times GS^2-0.089 \times (T-32)) \times 7 \times 10^6$$

whereby GS is the average grain size in meters, T is temperature in degree C., and 0.2% YS is in the unit of Pascal.

* * * * *